(12) United States Patent
Spinnler et al.

(10) Patent No.: US 9,308,068 B2
(45) Date of Patent: Apr. 12, 2016

(54) IMPLANT FOR PARASTOMAL HERNIA

(75) Inventors: Linda Spinnler, Prommiers (FR); Julie Lecuivre, Villefranche Sur Saone (FR); Alfredo Meneghin, Lyons (FR); Michel Therin, Lyons (FR)

(73) Assignee: Sofradim Production (FR)

( * ) Notice: Subject to any disclaimer, the term of this patent is extended or adjusted under 35 U.S.C. 154(b) by 1460 days.

(21) Appl. No.: 12/326,303

(22) Filed: Dec. 2, 2008

(65) Prior Publication Data

US 2009/0192532 A1   Jul. 30, 2009

Related U.S. Application Data

(60) Provisional application No. 61/005,131, filed on Dec. 3, 2007.

(51) Int. Cl.
| | | |
|---|---|---|
| A61B 17/08 | (2006.01) | |
| A61F 2/00 | (2006.01) | |
| D04B 21/12 | (2006.01) | |
| A61F 5/445 | (2006.01) | |

(52) U.S. Cl.
CPC .............. *A61F 2/0063* (2013.01); *D04B 21/12* (2013.01); *A61F 5/445* (2013.01); *A61F 2250/0036* (2013.01); *D10B 2403/0112* (2013.01); *D10B 2403/0213* (2013.01); *D10B 2501/0632* (2013.01); *D10B 2509/08* (2013.01)

(58) Field of Classification Search
CPC .................. A61F 2/0063; A61F 5/445; A61F 2250/0036; D10B 2509/08; D10B 2403/0213; D10B 2403/0112; D10B 2501/0632; D04B 21/12

USPC ............. 606/151, 193, 194; 623/23.72–23.74
See application file for complete search history.

(56) References Cited

U.S. PATENT DOCUMENTS

| | | | |
|---|---|---|---|
| 1,187,158 A | | 6/1916 | McGinley |
| 3,364,200 A | | 11/1961 | Ashton et al. |
| 3,118,294 A | | 1/1964 | Van Laethem |
| 3,124,136 A | | 3/1964 | Usher |
| 3,272,204 A | * | 9/1966 | Artandi et al. ................ 606/151 |
| 3,276,448 A | | 10/1966 | Kronenthal et al. |

(Continued)

FOREIGN PATENT DOCUMENTS

| | | |
|---|---|---|
| CA | 1317836 | 5/1993 |
| EP | 0 248 544 | 12/1987 |

(Continued)

OTHER PUBLICATIONS

Ellouali M, et al., "Antitumor activity of low molecular weight fucans extracted from brown seaweed Ascophyllum Nodosum", *Anticancer Res.* Nov.-Dec. 1993; 12(6A):2011-9.

(Continued)

*Primary Examiner* — Gregory Anderson
*Assistant Examiner* — Son Dang

(57) ABSTRACT

An implant for the prevention or treatment of a hernia in the proximity of an organ stoma formed in an abdominal wall includes a porous structure having a surface intended to face the abdominal cavity covered by a first film of anti-adhesive material. The porous structure includes a first part intended to be in contact with a stoma organ and having a first thickness, and a second part having a second thickness greater than the first thickness, the first part including a surface intended to face the abdominal wall covered by a second film of anti-adhesive material.

40 Claims, 8 Drawing Sheets

(56) References Cited

U.S. PATENT DOCUMENTS

| | | | |
|---|---|---|---|
| 3,320,649 A | 5/1967 | Naimer | |
| 3,570,482 A | 3/1971 | Emoto et al. | |
| 4,006,747 A | 2/1977 | Kronenthal et al. | |
| 4,060,081 A | 11/1977 | Yannas et al. | |
| 4,173,131 A | 11/1979 | Pendergrass et al. | |
| 4,193,137 A | 3/1980 | Heck | |
| 4,248,064 A | 2/1981 | Odham | |
| 4,294,241 A | 10/1981 | Miyata | |
| 4,307,717 A | 12/1981 | Hymes et al. | |
| 4,338,800 A | 7/1982 | Matsuda | |
| 4,476,697 A | 10/1984 | Schäfer et al. | |
| 4,487,865 A | 12/1984 | Balazs et al. | |
| 4,500,676 A | 2/1985 | Balazs et al. | |
| 4,511,653 A | 4/1985 | Play et al. | |
| 4,527,404 A | 7/1985 | Nakagaki et al. | |
| 4,591,501 A | 5/1986 | Cioca | |
| 4,597,762 A | 7/1986 | Walter et al. | |
| 4,603,695 A | 8/1986 | Ikada et al. | |
| 4,631,932 A | 12/1986 | Sommers | |
| 4,670,014 A | 6/1987 | Huc et al. | |
| 4,709,562 A | 12/1987 | Matsuda | |
| 4,748,078 A | 5/1988 | Doi et al. | |
| 4,759,354 A | 7/1988 | Quarfoot | |
| 4,769,038 A | 9/1988 | Bendavid et al. | |
| 4,796,603 A | 1/1989 | Dahlke et al. | |
| 4,813,942 A | 3/1989 | Alvarez | |
| 4,841,962 A | 6/1989 | Berg et al. | |
| 4,854,316 A | 8/1989 | Davis | |
| 4,925,294 A | 5/1990 | Geshwind et al. | |
| 4,931,546 A | 6/1990 | Tardy et al. | |
| 4,942,875 A | 7/1990 | Hlavacek et al. | |
| 4,948,540 A | 8/1990 | Nigam | |
| 4,950,483 A | 8/1990 | Ksander et al. | |
| 4,970,298 A | 11/1990 | Silver et al. | |
| 5,002,551 A | 3/1991 | Linsky et al. | |
| 5,147,374 A | 9/1992 | Fernandez | |
| 5,162,430 A | 11/1992 | Rhee et al. | |
| 5,171,273 A | 12/1992 | Silver et al. | |
| 5,176,692 A * | 1/1993 | Wilk et al. | 606/151 |
| 5,192,301 A | 3/1993 | Kamiya et al. | |
| 5,196,185 A | 3/1993 | Silver et al. | |
| 5,201,764 A | 4/1993 | Kelman et al. | |
| 5,206,028 A | 4/1993 | Li | |
| 5,217,493 A | 6/1993 | Raad et al. | |
| 5,254,133 A | 10/1993 | Seid | |
| 5,256,418 A | 10/1993 | Kemp et al. | |
| 5,263,983 A | 11/1993 | Yoshizato et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,334,527 A | 8/1994 | Brysk | |
| 5,339,657 A | 8/1994 | McMurray | |
| 5,350,583 A | 9/1994 | Yoshizato et al. | |
| 5,356,432 A | 10/1994 | Rutkow et al. | |
| 5,368,549 A | 11/1994 | McVicker | |
| 5,376,375 A | 12/1994 | Rhee et al. | |
| 5,376,376 A | 12/1994 | Li | |
| 5,397,331 A | 3/1995 | Himpens et al. | |
| 5,399,361 A | 3/1995 | Song et al. | |
| 5,413,791 A | 5/1995 | Rhee et al. | |
| 5,425,740 A * | 6/1995 | Hutchinson, Jr. | 606/157 |
| 5,428,022 A | 6/1995 | Palefsky et al. | |
| 5,433,996 A | 7/1995 | Kranzler et al. | |
| 5,441,491 A | 8/1995 | Verschoor et al. | |
| 5,441,508 A | 8/1995 | Gazielly et al. | |
| 5,456,693 A | 10/1995 | Conston et al. | |
| 5,456,711 A | 10/1995 | Hudson | |
| 5,466,462 A | 11/1995 | Rosenthal et al. | |
| 5,480,644 A | 1/1996 | Freed | |
| 5,487,895 A | 1/1996 | Dapper et al. | |
| 5,490,984 A | 2/1996 | Freed | |
| 5,512,291 A | 4/1996 | Li | |
| 5,512,301 A | 4/1996 | Song et al. | |
| 5,514,181 A | 5/1996 | Light et al. | |
| 5,522,840 A | 6/1996 | Krajicek | |
| 5,523,348 A | 6/1996 | Rhee et al. | |
| 5,536,656 A | 7/1996 | Kemp et al. | |
| 5,543,441 A | 8/1996 | Rhee et al. | |
| 5,565,210 A | 10/1996 | Rosenthal et al. | |
| 5,567,806 A | 10/1996 | Abdul-Malak et al. | |
| 5,569,273 A | 10/1996 | Titone et al. | |
| RE35,399 E | 12/1996 | Eisenberg | |
| 5,593,441 A | 1/1997 | Lichtenstein et al. | |
| 5,595,621 A | 1/1997 | Light et al. | |
| 5,601,571 A | 2/1997 | Moss | |
| 5,607,590 A | 3/1997 | Shimizu | |
| 5,614,587 A | 3/1997 | Rhee et al. | |
| 5,618,551 A | 4/1997 | Tardy et al. | |
| 5,634,931 A * | 6/1997 | Kugel | 606/151 |
| 5,639,796 A | 6/1997 | Lee | |
| 5,665,391 A | 9/1997 | Lea | |
| 5,667,839 A | 9/1997 | Berg | |
| 5,681,568 A | 10/1997 | Goldin et al. | |
| 5,686,115 A | 11/1997 | Vournakis et al. | |
| 5,690,675 A | 11/1997 | Sawyer et al. | |
| 5,695,525 A * | 12/1997 | Mulhauser et al. | 606/151 |
| 5,697,978 A | 12/1997 | Sgro | |
| 5,700,476 A | 12/1997 | Rosenthal et al. | |
| 5,700,477 A | 12/1997 | Rosenthal et al. | |
| 5,709,934 A | 1/1998 | Bell et al. | |
| 5,716,409 A | 2/1998 | Debbas | |
| 5,720,981 A | 2/1998 | Eisinger | |
| 5,732,572 A | 3/1998 | Litton | |
| 5,749,895 A | 5/1998 | Sawyer et al. | |
| 5,752,974 A | 5/1998 | Rhee et al. | |
| 5,766,246 A * | 6/1998 | Mulhauser et al. | 606/151 |
| 5,766,631 A | 6/1998 | Arnold | |
| 5,769,864 A * | 6/1998 | Kugel | 606/151 |
| 5,771,716 A | 6/1998 | Schlussel | |
| 5,785,983 A | 7/1998 | Furlan et al. | |
| 5,800,541 A | 9/1998 | Rhee et al. | |
| 5,814,328 A | 9/1998 | Gunasekaran | |
| 5,833,705 A | 11/1998 | Ken et al. | |
| 5,840,011 A | 11/1998 | Landgrebe et al. | |
| 5,861,034 A | 1/1999 | Taira et al. | |
| 5,863,984 A | 1/1999 | Doillon et al. | |
| 5,869,080 A | 2/1999 | McGregor et al. | |
| 5,871,767 A | 2/1999 | Dionne et al. | |
| 5,876,444 A | 3/1999 | Lai | |
| 5,891,558 A | 4/1999 | Bell et al. | |
| 5,899,909 A | 5/1999 | Claren et al. | |
| 5,906,937 A | 5/1999 | Sugiyama et al. | |
| 5,910,149 A * | 6/1999 | Kuzmak | 606/157 |
| 5,911,731 A | 6/1999 | Pham et al. | |
| 5,916,225 A * | 6/1999 | Kugel | 606/151 |
| 5,919,232 A * | 7/1999 | Chaffringeon et al. | 424/423 |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,022 A | 10/1999 | Huxel | |
| RE36,370 E | 11/1999 | Li | |
| 5,993,844 A | 11/1999 | Abraham et al. | |
| 5,994,325 A | 11/1999 | Roufa et al. | |
| 5,997,895 A | 12/1999 | Narotam et al. | |
| 6,001,895 A | 12/1999 | Harvey et al. | |
| 6,008,292 A | 12/1999 | Lee et al. | |
| 6,015,844 A | 1/2000 | Harvey et al. | |
| 6,039,686 A | 3/2000 | Kovac | |
| 6,042,534 A | 3/2000 | Gellman et al. | |
| 6,042,592 A * | 3/2000 | Schmitt | 606/151 |
| 6,043,089 A | 3/2000 | Sugiyama et al. | |
| 6,051,425 A | 4/2000 | Morota et al. | |
| 6,056,688 A | 5/2000 | Benderev et al. | |
| 6,056,970 A | 5/2000 | Greenawalt et al. | |
| 6,057,148 A | 5/2000 | Sugiyama et al. | |
| 6,063,396 A | 5/2000 | Kelleher | |
| 6,066,776 A | 5/2000 | Goodwin et al. | |
| 6,066,777 A | 5/2000 | Benchetrit | |
| 6,071,292 A | 6/2000 | Makower et al. | |
| 6,077,281 A * | 6/2000 | Das | 606/151 |
| 6,080,194 A | 6/2000 | Pachence et al. | |

(56) References Cited

U.S. PATENT DOCUMENTS

| | | | |
|---|---|---|---|
| 6,083,522 A | 7/2000 | Chu et al. | |
| 6,120,539 A | 9/2000 | Eldridge et al. | |
| 6,132,765 A | 10/2000 | DiCosmo et al. | |
| 6,143,037 A | 11/2000 | Goldstein et al. | |
| 6,153,292 A | 11/2000 | Bell et al. | |
| 6,165,488 A | 12/2000 | Tardy et al. | |
| 6,171,318 B1 * | 1/2001 | Kugel et al. | 606/151 |
| 6,174,320 B1 * | 1/2001 | Kugel et al. | 606/151 |
| 6,176,863 B1 * | 1/2001 | Kugel et al. | 606/151 |
| 6,179,872 B1 | 1/2001 | Bell et al. | |
| 6,197,325 B1 | 3/2001 | MacPhee et al. | |
| 6,197,934 B1 | 3/2001 | DeVore et al. | |
| 6,197,935 B1 | 3/2001 | Doillon et al. | |
| 6,210,439 B1 * | 4/2001 | Firmin et al. | 623/8 |
| 6,221,109 B1 | 4/2001 | Geistlich et al. | |
| 6,224,616 B1 * | 5/2001 | Kugel | 606/151 |
| 6,241,768 B1 | 6/2001 | Agarwal et al. | |
| 6,258,124 B1 | 7/2001 | Darois et al. | |
| 6,262,332 B1 | 7/2001 | Ketharanathan | |
| 6,264,702 B1 | 7/2001 | Ory et al. | |
| 6,267,772 B1 * | 7/2001 | Mulhauser et al. | 606/151 |
| 6,277,397 B1 | 8/2001 | Shimizu | |
| 6,280,453 B1 * | 8/2001 | Kugel et al. | 606/151 |
| 6,287,316 B1 | 9/2001 | Agarwal et al. | |
| 6,290,708 B1 * | 9/2001 | Kugel et al. | 606/151 |
| 6,306,424 B1 | 10/2001 | Vyakarnam et al. | |
| 6,312,474 B1 | 11/2001 | Francis et al. | |
| 6,328,686 B1 | 12/2001 | Kovac | |
| 6,334,872 B1 | 1/2002 | Termin et al. | |
| 6,383,201 B1 * | 5/2002 | Dong | 606/151 |
| 6,391,333 B1 | 5/2002 | Li et al. | |
| 6,391,939 B2 | 5/2002 | Tayot et al. | |
| 6,408,656 B1 * | 6/2002 | Ory et al. | 66/195 |
| 6,410,044 B1 | 6/2002 | Chudzik et al. | |
| 6,413,742 B1 | 7/2002 | Olsen et al. | |
| 6,428,978 B1 | 8/2002 | Olsen et al. | |
| 6,436,030 B2 * | 8/2002 | Rehil | 600/37 |
| 6,440,167 B2 | 8/2002 | Shimizu | |
| 6,443,964 B1 | 9/2002 | Ory et al. | |
| 6,447,551 B1 | 9/2002 | Goldmann | |
| 6,447,802 B2 | 9/2002 | Sessions et al. | |
| 6,448,378 B2 | 9/2002 | DeVore et al. | |
| 6,451,032 B1 | 9/2002 | Ory et al. | |
| 6,451,301 B1 | 9/2002 | Sessions et al. | |
| 6,454,787 B1 | 9/2002 | Maddalo et al. | |
| 6,477,865 B1 | 11/2002 | Matsumoto | |
| 6,479,072 B1 | 11/2002 | Morgan et al. | |
| 6,500,464 B2 | 12/2002 | Ceres et al. | |
| 6,509,031 B1 | 1/2003 | Miller et al. | |
| 6,511,958 B1 | 1/2003 | Atkinson et al. | |
| 6,514,286 B1 | 2/2003 | Leatherbury et al. | |
| 6,514,514 B1 | 2/2003 | Atkinson et al. | |
| 6,540,773 B2 | 4/2003 | Dong | |
| 6,541,023 B1 | 4/2003 | Andre et al. | |
| 6,548,077 B1 | 4/2003 | Gunasekaran | |
| 6,554,855 B1 | 4/2003 | Dong | |
| 6,559,119 B1 | 5/2003 | Burgess et al. | |
| 6,566,345 B2 | 5/2003 | Miller et al. | |
| 6,575,988 B2 * | 6/2003 | Rousseau | 606/151 |
| 6,576,019 B1 | 6/2003 | Atala | |
| 6,596,002 B2 * | 7/2003 | Therin et al. | 606/151 |
| 6,596,304 B1 | 7/2003 | Bayon et al. | |
| 6,599,323 B2 | 7/2003 | Melican et al. | |
| 6,599,524 B2 | 7/2003 | Li et al. | |
| 6,599,690 B1 | 7/2003 | Abraham et al. | |
| 6,613,348 B1 | 9/2003 | Jain | |
| 6,623,963 B1 | 9/2003 | Müller et al. | |
| 6,630,414 B1 | 10/2003 | Matsumoto | |
| 6,638,284 B1 | 10/2003 | Rousseau et al. | |
| 6,652,594 B2 | 11/2003 | Francis et al. | |
| 6,653,450 B1 | 11/2003 | Berg et al. | |
| 6,656,206 B2 * | 12/2003 | Corcoran et al. | 606/213 |
| 6,660,280 B1 | 12/2003 | Allard et al. | |
| 6,669,735 B1 * | 12/2003 | Pelissier | 623/23.74 |
| 6,682,760 B2 | 1/2004 | Noff et al. | |
| 6,685,714 B2 * | 2/2004 | Rousseau | 606/151 |
| 6,706,684 B1 | 3/2004 | Bayon et al. | |
| 6,706,690 B2 | 3/2004 | Reich et al. | |
| 6,719,795 B1 | 4/2004 | Cornwall et al. | |
| 6,723,335 B1 | 4/2004 | Moehlenbruck et al. | |
| 6,730,299 B1 | 5/2004 | Tayot et al. | |
| 6,743,435 B2 | 6/2004 | DeVore et al. | |
| 6,755,868 B2 * | 6/2004 | Rousseau | 623/23.64 |
| 6,773,723 B1 | 8/2004 | Spiro et al. | |
| 6,790,213 B2 * | 9/2004 | Cherok et al. | 606/151 |
| 6,790,454 B1 | 9/2004 | Abdul Malak et al. | |
| 6,800,082 B2 * | 10/2004 | Rousseau | 606/151 |
| 6,833,408 B2 | 12/2004 | Sehl et al. | |
| 6,835,336 B2 | 12/2004 | Watt | |
| 6,852,330 B2 | 2/2005 | Bowman et al. | |
| 6,869,938 B1 | 3/2005 | Schwartz et al. | |
| 6,893,653 B2 | 5/2005 | Abraham et al. | |
| 6,896,904 B2 | 5/2005 | Spiro et al. | |
| 6,936,276 B2 | 8/2005 | Spiro et al. | |
| 6,939,562 B2 | 9/2005 | Spiro et al. | |
| 6,949,625 B2 | 9/2005 | Tayot | |
| 6,966,918 B1 | 11/2005 | Schuldt-Hempe | |
| 6,971,252 B2 * | 12/2005 | Therin et al. | 66/170 |
| 6,974,679 B2 | 12/2005 | Andre et al. | |
| 6,974,862 B2 | 12/2005 | Ringeisen et al. | |
| 6,977,231 B1 | 12/2005 | Matsuda | |
| 6,988,386 B1 | 1/2006 | Okawa et al. | |
| 7,025,063 B2 | 4/2006 | Snitkin et al. | |
| 7,041,868 B2 | 5/2006 | Greene et al. | |
| RE39,172 E | 7/2006 | Bayon et al. | |
| 7,098,315 B2 | 8/2006 | Schaufler | |
| 7,175,852 B2 | 2/2007 | Simmoteit et al. | |
| 7,192,604 B2 | 3/2007 | Brown et al. | |
| 7,207,962 B2 | 4/2007 | Anand et al. | |
| 7,214,765 B2 | 5/2007 | Ringeisen et al. | |
| 7,226,611 B2 | 6/2007 | Yura et al. | |
| 7,229,453 B2 | 6/2007 | Anderson et al. | |
| 7,594,921 B2 * | 9/2009 | Browning | 606/151 |
| 7,670,380 B2 * | 3/2010 | Cauthen, III | 623/17.16 |
| 2001/0008930 A1 | 7/2001 | Tayot et al. | |
| 2002/0095218 A1 | 7/2002 | Carr, Jr. et al. | |
| 2002/0116070 A1 | 8/2002 | Amara et al. | |
| 2003/0013989 A1 | 1/2003 | Obermiller et al. | |
| 2003/0023316 A1 | 1/2003 | Brown et al. | |
| 2003/0086975 A1 | 5/2003 | Ringeisen | |
| 2003/0100954 A1 | 5/2003 | Schuldt-Hempe et al. | |
| 2003/0114937 A1 | 6/2003 | Leatherbury et al. | |
| 2003/0133967 A1 | 7/2003 | Ruszczak et al. | |
| 2003/0212460 A1 | 11/2003 | Darois et al. | |
| 2003/0225355 A1 | 12/2003 | Butler | |
| 2003/0232746 A1 | 12/2003 | Lamberti et al. | |
| 2004/0034373 A1 | 2/2004 | Schuldt-Hempe et al. | |
| 2004/0054406 A1 | 3/2004 | Dubson et al. | |
| 2004/0059356 A1 | 3/2004 | Gingras | |
| 2004/0101546 A1 | 5/2004 | Gorman et al. | |
| 2004/0138762 A1 * | 7/2004 | Therin et al. | 623/23.75 |
| 2004/0172048 A1 | 9/2004 | Browning | |
| 2004/0215219 A1 | 10/2004 | Eldridge et al. | |
| 2005/0002893 A1 | 1/2005 | Goldmann | |
| 2005/0010306 A1 | 1/2005 | Priewe et al. | |
| 2005/0021058 A1 | 1/2005 | Negro | |
| 2005/0085924 A1 | 4/2005 | Darois et al. | |
| 2005/0113849 A1 | 5/2005 | Popadiuk et al. | |
| 2005/0113938 A1 | 5/2005 | Jamiolkowski et al. | |
| 2005/0137512 A1 | 6/2005 | Campbell et al. | |
| 2005/0142161 A1 | 6/2005 | Freeman et al. | |
| 2005/0148963 A1 | 7/2005 | Brennan | |
| 2005/0175659 A1 | 8/2005 | Macomber et al. | |
| 2005/0228408 A1 | 10/2005 | Fricke et al. | |
| 2005/0232979 A1 | 10/2005 | Shoshan | |
| 2005/0244455 A1 | 11/2005 | Greenawalt | |
| 2005/0267521 A1 | 12/2005 | Forsberg | |
| 2005/0288691 A1 | 12/2005 | Leiboff | |
| 2006/0094318 A1 | 5/2006 | Matsuda et al. | |
| 2006/0135921 A1 | 6/2006 | Wiercinski et al. | |
| 2006/0147501 A1 | 7/2006 | Hillas et al. | |
| 2006/0167561 A1 | 7/2006 | Odar et al. | |
| 2006/0216320 A1 | 9/2006 | Kitazono et al. | |
| 2006/0252981 A1 | 11/2006 | Matsuda et al. | |

(56) References Cited

U.S. PATENT DOCUMENTS

| | | | |
|---|---|---|---|
| 2007/0031474 A1 | 2/2007 | Tayot | |
| 2007/0161109 A1 | 7/2007 | Archibald et al. | |
| 2007/0280990 A1 | 12/2007 | Stopek | |
| 2007/0297987 A1* | 12/2007 | Stad et al. | 424/9.4 |
| 2007/0299538 A1* | 12/2007 | Roeber | 623/23.72 |

FOREIGN PATENT DOCUMENTS

| | | |
|---|---|---|
| EP | 0 276 890 | 8/1988 |
| EP | 0 372 969 | 6/1990 |
| EP | 0 544 485 | 6/1993 |
| EP | 0552576 A1 | 7/1993 |
| EP | 0 614 650 | 9/1994 |
| EP | 0621014 A1 | 10/1994 |
| EP | 0 625 891 | 11/1994 |
| EP | 0 693 523 | 1/1996 |
| EP | 0 705 878 | 4/1996 |
| EP | 0 797 962 | 3/1997 |
| EP | 0 774 240 | 5/1997 |
| EP | 0 827 724 | 3/1998 |
| EP | 0 895 762 | 2/1999 |
| EP | 0 898 944 | 3/1999 |
| EP | 0 637 452 | 10/1999 |
| EP | 1 017 415 | 7/2000 |
| EP | 1 052 319 | 11/2000 |
| EP | 1 055 757 | 11/2000 |
| EP | 1 216 717 | 6/2002 |
| EP | 1 216 718 | 6/2002 |
| EP | 1 315 468 | 6/2003 |
| EP | 1382728 A1 | 1/2004 |
| EP | 1 484 070 | 12/2004 |
| EP | 1 561 480 | 8/2005 |
| EP | 1 782 848 | 5/2007 |
| FR | 2244853 A1 | 4/1975 |
| FR | 2257262 A1 | 8/1975 |
| FR | 2453231 A1 | 10/1980 |
| FR | 2715405 A1 | 7/1995 |
| FR | 2744906 A1 | 8/1997 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2 051 153 | 1/1981 |
| JP | 03032677 | 2/1991 |
| JP | 05237128 | 9/1993 |
| JP | 09137380 | 5/1997 |
| WO | WO 89/02445 | 3/1989 |
| WO | WO 89/08467 | 9/1989 |
| WO | WO 90/12551 | 11/1990 |
| WO | WO 92/06639 | 4/1992 |
| WO | WO 92/20349 | 11/1992 |
| WO | WO 93/11805 | 6/1993 |
| WO | WO 93/18174 | 9/1993 |
| WO | WO 94/17747 | 8/1994 |
| WO | WO 95/07666 | 3/1995 |
| WO | WO 95/18638 | 7/1995 |
| WO | WO 95/32687 | 12/1995 |
| WO | WO 96/03091 | 2/1996 |
| WO | WO 96/08277 | 3/1996 |
| WO | WO 96/09795 | 4/1996 |
| WO | WO 96/14805 | 5/1996 |
| WO | WO 96/41588 | 12/1996 |
| WO | WO 97/35533 | 10/1997 |
| WO | WO 98/35632 | 8/1998 |
| WO | WO 98/49967 | 11/1998 |
| WO | WO 99/05990 | 2/1999 |
| WO | WO 99/06080 | 2/1999 |
| WO | WO 9906079 | 2/1999 |
| WO | WO 99/51163 | 10/1999 |
| WO | WO 00/16821 | 3/2000 |
| WO | WO00/67663 A | 11/2000 |
| WO | WO 01/15625 | 3/2001 |
| WO | WO 01/80773 | 11/2001 |
| WO | WO 02/07648 | 1/2002 |
| WO | WO 02/078568 | 10/2002 |
| WO | WO 03/002168 | 1/2003 |
| WO | WO 2004/004600 | 1/2004 |
| WO | WO2004/071349 A | 8/2004 |
| WO | WO 2004/078120 | 9/2004 |
| WO | WO2004/103212 A | 12/2004 |
| WO | WO 2005/013863 | 2/2005 |
| WO | WO 2005/018698 | 3/2005 |
| WO | WO 2005/105172 | 11/2005 |
| WO | WO 2005/11280 | 12/2005 |
| WO | WO 2006/018552 | 2/2006 |
| WO | WO 2006/023444 | 3/2006 |
| WO | WO 2007/048099 | 4/2007 |

OTHER PUBLICATIONS

Malette et al., Chitosan, a new hemostatic, *Ann Th. Surg.* 1983, 36:55-58.

Langenbech Mr, et al., "Comparison of biomaterials in the early postoperative period", *Surg Endosc.* 2003; 17(7):1105-9.

Bracco P., et al., "Comparison of polypropylene and polyethylene terephthalate (Dacron) meshes for abdominal wall hernia repair: a chemical and morphological study", *Hernia* 2005, 9(1):51-55.

Klinge U, et al., "Foreign body reaction to meshes used for the repair of abdominal wall hernias", *Eur J. Surg* 1999; 165:665-73.

Logeart D, et al., "Fucans, sulfated polysaccharides extracted from brown seaweeds, inhibit vascular smooth muscle cell proliferation. II. Degradation and molecular weight effect," *Eur J Cell Biol.* Dec. 1997; 74(4):385-90.

Haneji K, et al.., "Fucoidan extracted from Cladosiphon Okamuranus Tokida induces apoptosis of human T-cell leukemia virus type 1-infected T-cell lines and primary adult T-cell leukemia cells", *Nutrition and Cancer*, 2005; 52(2):189-201.

Junge K, et al., "Functional and morphologic properties of a modified mesh for inguinal hernia repair", *World J Surg* 2002; 26:1472-80.

Klinge, et al., "Functional and Morphological Evaluation of a Low-Weight, Monofilament Polypropylene Mesh for Hernia Repair", *J. Biomed Mater Res* 2002 63:129-136.

Welty G, et al., "Functional impairment and complaints following incisional hernia repair with different polypropylene meshes", *Hernia* 2001;5:142-7.

Varum Km et al., "In vitro degradation rates of partially N-acetylated chitosans in human serum", *Carbohydrate Research*, 1997, 299:99-101.

Haroun-Bouhedja F, et al., "In vitro effects of fucans on MDA-MB231 tumor cell adhesion and invasion", *Anticancer Res.* Jul.-Aug. 2002;22(4):2285-92.

Scheidbach H, et al., "In vivo studies comparing the biocompatibility of various polypropylene meshes and their handling properties during endoscopic total extraperitoneal (TEP) patchplasty: an experimental study in pigs", *Surg Endosc* 2004; 18(2):211-20.

Blondin C, et al., "Inhibition of complement activation by natural sulfated polysaccharides (fucans) from brown seaweed", *Molecular Immuol.* Mar. 1994; 31(4):247-53.

Zvyagintseva Tn, et al., "Inhibition of complement activation by water-soluble polysaccharides of some far-eastern brown seaweeds", *Comparative Biochem and Physiol* Jul. 2000; 126(3):209-15.

Rosen M, et al., "Laparoscopic component separation in the single-stage treatment of infected abdominal wall prosthetic removal", *Hernia*, 2007 11:435-440.

Amid P.K., "Lichtenstein tension-free hernioplasty: Its inception, evolution, and principles", *Hernia* 2004; 8:1-7.

Boisson-Vidal C, et al., "Neoangiogenesis induced by progenitor endothelial cells: effect of fucoidan from marine algae", *Cardiovascular & Hematological Agents in Medicinal Chem.* Jan. 2007; 5(1):67-77.

O'Dwyer Pj, et al., :Randomized clinical trial assessing impact of a lightweight or heavyweight mesh on chronic pain after inguinal hernia repair, *Br J Surg.* 2005; 92(2):166-70.

(56) References Cited

OTHER PUBLICATIONS

Muzzarelli, et al., "Reconstruction of parodontal tissue with chitosan", *Biomatetials* 1989, 10:598-604.

Haroun-Bouhedja F, et al., "Relationship between sulfate groups and biological activities of fucans", *Thrombosis Res.* Dec. 1, 2000, 100(5):453-9.

Blondin C, et al., "Relationships between chemical characteristics and anticomplementary activity of fucans", *Biomaterials*. Mar. 1996; 17(6):597-603.

Strand Sp, et al., "Screening of chitosans and conditions for bacterial flocculation", *Biomacromolecules*, 2001, 2:126-133.

Kanabar V, et al., "Some structural determinants of the antiproliferative effect of heparin-like molecules on human airway smooth muscle", *Br J Pharmacol*. Oct. 2005; 146(3):307-7.

Hirano et al., "The blood biocompatibility of chitosan and N-acylchitosans", *J Biomed. Mater. Res.* 1985, 19:413-417.

Rao S.B., et al., "Use of chitosan as a biomaterial: studies on its safety and haemostatic potential", *J. Biomed. Mater. Res.* 1997, 34:21-28.

Prokop A, et al., "Water soluble polymers for immunoisolation I: complex coacevation and cytotoxicity", *Advances in Polymer Science*, 1998 136:1-51.

Collins et al., "Use of collagen film as a dural substitute: Preliminary Animal Studies", Journal of Biomedical Materials Research, vol. 25, pp. 267-276(1991).

Preliminary Search Report from French Patent Office dated Dec. 20, 2006.

International Search Report for PCTIB08003761 date of completion is May 20, 2009 (3 pages).

\* cited by examiner

IMPLANT FOR PARASTOMAL HERNIA

CROSS-REFERENCE TO RELATED APPLICATIONS

This application claims the benefit of U.S. Provisional Application No. 61/005,131, filed Dec. 3, 2007.

BACKGROUND

1. Technical Field

The present disclosure relates to an implant suitable for use in the prevention and/or treatment of hernias that may occur in the area of a stoma, particularly one formed in the abdominal wall.

2. Description of Related Art

Stomas are openings formed in a wall, for example the abdominal wall, for joining a hollow organ, for example the intestine, to the skin. Such an operation proves necessary, for example in cases of cancer of the rectum or Crohn's disease, to create an artificial anus for example, during which operation the diseased part of the intestine is resected and the healthy intestine is exteriorized at the skin. In this case, the stoma is formed in the abdominal wall. FIG. 1 is a schematic illustration of the human digestive tract. This diagram shows the stomach 1, the small intestine 2 and the colon 3. The broken lines represent the part 3a of the colon that is diseased and has been removed during the surgical procedure. The healthy part 3b of the colon now opens to the outside at the stoma 4 formed in the abdominal wall. Depending on the extent of the diseased part of the colon, the stomas can be formed in the area of the ileum 5 (ileostomy) or of the colon (colostomy), as shown in FIG. 1. Stomas can also be formed in the area of the ureters (ureterostomy).

After operations of this kind, hernias may develop around the stoma, that is to say in the area of the peristomal wall. A weakening of the wall around the stoma may therefore result in the appearance of a parastomal hernia. To treat these parastomal hernias, prostheses are implanted that are designed to strengthen the abdominal wall inside the patient, in the area of the stoma. The implantation of these prostheses can be intraperitoneal, that is to say within the actual abdominal wall, or retroperitoneal, resting against the abdominal wall.

Prostheses for treating parastomal hernias have been described in the document WO2004/071349. However, these prostheses are not entirely satisfactory, particularly since they are not adapted to all types of stomas that are formed, particularly indirect stomas.

The reason is that, for example in the case of the colon, several stoma configurations can be formed: the direct stoma, as shown in FIG. 2, in which the colon 3 issuing from the abdominal cavity 8 is perpendicular to the abdominal wall 7 and hence to the skin 6 prior to its exteriorization, or the indirect stoma, as shown in FIG. 3, in which the colon 3 is caused to form a bend within the abdominal cavity 8 prior to its exteriorization, the colon thus having a part 3c parallel to the abdominal wall 7. The indirect stoma avoids a situation where the internal part of the colon in the area of the stoma becomes invaginated and exteriorizes.

There is therefore a need for a parastomal prosthesis able to protect the intestine and hollow organs and to effectively strengthen the abdominal wall regardless of the type of stoma that has been formed.

SUMMARY

The present disclosure aims to meet this need by making available an implant that has specific surfaces able to protect the hollow organs, such as the intestine, regardless of the stoma that has been formed, and at the same time to effectively strengthen the abdominal wall.

The subject matter of the present disclosure is an implant for the prevention or treatment of a hernia formed in the abdominal wall in the proximity of a stoma of an organ, having a porous structure including a surface intended to face the abdominal cavity covered by a first film of anti-adhesive material, the porous structure including a first part intended to be in contact with the stoma organ and having a first thickness E1, and a second part having a second thickness E2 greater than the first thickness E1, the first part having a surface intended to face the abdominal wall covered by a second film of anti-adhesive material.

Thus, in the implant according to the disclosure, the first part of the porous structure, the part intended to be in contact with the stoma organ, for example in contact with the intestine, is covered by a film of anti-adhesive material on both of its surfaces. In one embodiment of the disclosure, the first and second films of anti-adhesive material are joined to form just one film, and the first part of the porous structure is totally enclosed within the film of anti-adhesive material. As will become clear from the explanations given later with reference to FIGS. 13 to 15, the stoma organ, for example the intestine, is protected irrespective of whether the stoma is a direct or indirect one, because the part of the implant able to come into contact with it is covered by a film of anti-adhesive material.

In the present application, an "implant" is understood as a biocompatible medical device that can be implanted in the human or animal body.

Within the meaning of the present application, the word "porous" is understood as the characteristic according to which a structure has pores or meshes, pockets, holes or orifices, that are open and are distributed uniformly or irregularly and promote all cell colonization. The pores can be present in all types of configurations, for example as spheres, channels, hexagonal forms.

According to one embodiment of the disclosure, the porous structure includes a sponge, a fibrous matrix or a combination of a sponge and of a fibrous matrix. For example, the sponge can be obtained by lyophilization of a gel, with pores being created during the lyophilization. The fibrous matrix can be any arrangement of yarns or yarn portions creating pores between the yarns and/or yarn portions. For example, the fibrous matrix can be a textile, for example obtained by knitting or weaving or according to a technique for producing a nonwoven.

In one embodiment of the present disclosure, the porous structure, for example the sponge and/or the fibrous matrix, has pores with dimensions ranging from approximately 0.1 to approximately 3 mm.

In one embodiment of the present disclosure, the porous structure includes a textile. For example, the porous structure can be composed of a textile.

According to one embodiment of the present disclosure, the thickness E1 of the first part of the porous structure ranges from approximately 0.15 to 0.50 mm. A relatively small thickness of this kind allows the abdominal wall to be strengthened without any risk of damaging the stoma organ, for example the intestine, which is in contact with the implant.

The first part of the porous structure may be a textile in the form of a knit. This knit may be a two-dimensional knit, in embodiments a knit having a thickness less than or equal to about 5 times the mean diameter of the yarns from which it is made, for example knitted on a warp knitting machine or raschel machine with the aid of two guide bars forming a knit with two surfaces, the knit being free of sheets of connecting yarns between its two opposite surfaces.

When the first part of porous structure is a two-dimensional knit as defined above, the pores are formed by the empty spaces situated between the constituent yarns of the knit, for example the meshes.

The constituent yarns of the knit that form the first part of porous structure can be chosen from among yarns made of biocompatible materials, bioabsorbable materials, non-bioabsorbable materials and their mixtures.

In the present application, the word "bioabsorbable" is understood as the characteristic according to which a material is absorbed by the biological tissues and disappears in vivo at the end of a given period, which can vary for example from one day to several months, depending on the chemical nature of the material.

Thus, examples of bioabsorbable materials suitable for the yarns forming the first part of porous structure are polylactic acid (PLA), polysaccharides, polycaprolactones (PCL), polydioxanones (PDO), trimethylene carbonates (TMC), polyvinyl alcohol (PVA), polyhydroxyalkanoates (PHA), polyamides, polyethers, oxidized cellulose, polyglycolic acid (PGA), copolymers of these materials and their mixtures.

Examples of non-bioabsorbable materials suitable for the yarns forming the first part of porous structure are polypropylenes, polyesters such as polyethylene terephthalates, polyamides, polyvinylidene fluoride, and their mixtures.

The yarns forming the first part of porous structure of the implant can, for example, be chosen from among monofilament yarns, multifilament yarns and their combinations. The multifilament yarn count may vary from about 40 to about 110 dtex. The monofilament yarns may also have a diameter from about 0.06 to about 0.15 mm.

In one embodiment of the present disclosure, the yarns forming the first part of the porous structure are monofilament yarns. Such monofilament yarns may pose less risk of sepsis than do multifilament yarns. In one embodiment of the present disclosure, the monofilament yarns are of polyethylene terephthalate.

A monofilament yarn suitable for the first textile part of the implant according to the present disclosure is, for example, a monofilament yarn with a diameter of approximately 0.08 mm, of polyethylene terephthalate.

The porous structure of the implant according to the present disclosure includes a second part with a thickness E2 greater than the thickness E1 of the first part. The second part of the porous structure may be designed to act as a reinforcement of the abdominal wall.

Thus, the value of the thickness E2 of the second part of porous structure can vary depending on the value of the thickness E1 of the first part of the structure, the value of the thickness E2 of the second part of porous structure may be greater than that of the value of the thickness E1 of the first part of porous structure. The second part of the porous structure may have mechanical strength superior to that of the first part of porous structure. For example, the second thickness E2 of the second part of the porous structure can range from approximately 0.40 to 3.00 mm.

As will become clear from the description that follows, the surface of the layer of porous structure intended to be placed facing the abdominal cavity is covered by a film of anti-adhesive material which prevents the organs and other viscera of the abdominal cavity from attaching themselves to the implant. This surface will be referred to hereinafter as the closed surface of the implant. By contrast, the surface of the second part of porous structure intended to be placed facing the abdominal wall is not covered by a film of anti-adhesive material and remains open to all cell colonization at the time of implantation. This surface will be referred to hereinafter as the open surface of the second part of the porous structure. This surface of the second part of the porous structure is intended to be placed resting against the abdominal wall. To permit better fixing of the implant to the abdominal wall, the open surface of the second part of porous structure can include fastening means, for example self-fixing ones, inherent to this surface.

Thus, by virtue of its porous character and its thickness, the second part of the porous structure of the implant according to the disclosure is especially adapted to promote tissue growth via its open surface after implantation. The cells of the abdominal wall deeply colonize the second part of the porous structure by way of its open surface placed facing the abdominal wall.

In one embodiment of the present disclosure, the second part of the porous structure is a textile in the form of a three-dimensional knit, for example as described in applications WO99/06080 and WO99/05990, the disclosures of which are incorporated herein by this reference in their entirety. Within the meaning of the present application, the term "three-dimensional knit" is understood as an assembly or arrangement of monofilament or multifilament yarns or a combination of these, obtained by knitting and having two opposite surfaces that are separated by a thickness, in embodiments greater than or equal to about 0.50 mm, the thickness including connecting yarns and pores.

Such a three-dimensional knit can be knitted, for example, on a warp knitting machine or double-bed raschel machine with the aid of several guide bars forming a knit that includes two opposite surfaces and a spacer. In the present application, the word "spacer" is understood as the set or sets of yarns that connect the two surfaces of a three-dimensional knit to each other, thereby constituting the thickness of a knit, as is described in WO99/06080 or in WO99/05990.

Thus, in the case where the second part of the porous structure is a three-dimensional knit as described above, the knitting structure can define within the thickness of the knit a multiplicity of transverse channels or pockets that may or may not be mutually parallel. These pockets or channels can be interconnected and thus allow the colonizing cells to pass from one pocket or channel to another. A second part of the porous structure of this type promotes good tissue growth after implantation.

The yarns constituting the second part of the porous structure of the implant according to the present disclosure can be chosen from among yarns made of biocompatible materials, bioabsorbable materials, non-bioabsorbable materials and their mixtures, already listed above for the first part of the porous structure.

Thus, examples of bioabsorbable materials suitable for the yarns forming the second part of the porous structure are polylactic acid (PLA), polysaccharides, polycaprolactones (PCL), polydioxanones (PDO), trimethylene carbonates (TMC), polyvinyl alcohol (PVA), polyhydroxyalkanoates (PHA), polyamides, polyethers, oxidized cellulose, polyglycolic acid (PGA), copolymers of these materials and their mixtures.

Examples of non-bioabsorbable materials suitable for the yarns forming the second part of the porous structure are polypropylenes, polyesters such as polyethylene terephthalates, polyamides, polyvinylidene fluoride, and their mixtures.

The yarns forming the second part of the porous structure can, for example, be chosen from among monofilament yarns, multifilament yarns and their combinations. The multifilament yarn count may vary from about 40 to about 110 dtex. The monofilament yarns may have a diameter of from about 0.06 to about 0.15 mm.

In one embodiment of the present disclosure, the yarns forming the first part of the porous structure are monofilament yarns. Such monofilament yarns may pose less risk of sepsis than do multifilament yarns. For example, the monofilament yarns are of polyethylene terephthalate.

A monofilament yarn suitable for the second part of the porous structure of the implant according to the present disclosure is, for example, a monofilament yarn with a diameter of approximately 0.08 mm, of polyethylene terephthalate.

In one embodiment of the present disclosure, the second part of the porous structure has, on its open surface intended to face the abdominal wall, means of fastening the second part to the abdominal wall. These fastening means can be chosen from among elements that are integrally formed on the second textile part, such as loops and barbs, or from among elements joined to the surface of the second textile part, such as a rough covering, hooks, threads or clips fixed on the surface of the second textile part.

In one embodiment of the present disclosure, the fastening means are chosen from among loops, barbs and their mixtures. In such a case, the loops and barbs can be obtained from yarns or portions of yarns that are woven and/or knitted directly for example, with the three-dimensional knit forming the second part of the porous structure. For example, in order to obtain barbs, it is possible to use hot-melt yarns such as are described in the application WO01/81667, the contents of which are herein incorporated by reference in its entirety.

In the embodiment of the present disclosure in which the first part of the porous structure is in the form of a two-dimensional knit and the second part of the porous structure is in the from of a three-dimensional knit, the two knits, i.e. two-dimensional and three-dimensional, can be manufactured separately then joined together by at least one seam, for example, in order to form the layer of porous structure of the implant.

In another embodiment, the two-dimensional knit and the three-dimensional knit are knitted together on the same knitting machine and constitute a textile made in one piece, for example by using supplementary guide bars for the three-dimensional knit and/or different yarn runs for producing each of the two knits. In such an embodiment of the present disclosure, the porous structure layer of the implant according to the disclosure is composed of a textile formed in one piece, the textile having a two-dimensional zone, corresponding to the first part of the porous structure, and one or more three-dimensional zones, corresponding to the second part of the porous structure. In such an embodiment, it is possible to form a selvage at the passage from a two-dimensional zone to a three-dimensional zone with a view to forming a smooth connection between the two parts, such that the difference in thickness between the two parts does not form a step that could damage the biological tissue situated in the proximity of the implant.

The layer of porous structure of the implant according to the present disclosure is covered, on its second surface intended to face the abdominal cavity, by a first film of anti-adhesive material. Moreover, the first part of the porous structure is covered, on its surface intended to face the abdominal wall, by a second film of anti-adhesive material.

Within the meaning of the present application, the term "anti-adhesive material" is understood as a smooth and non-porous biocompatible material that prevents the organs and other viscera of the abdominal cavity from attaching themselves to the implant.

The anti-adhesive material forming the first film can be identical to or different from the material forming the second film.

In one embodiment of the present disclosure, the anti-adhesive material constituting the first and/or second film(s) is chosen from among bioabsorbable materials, non-bioabsorbable materials and their mixtures.

In one embodiment of the present disclosure, the bioabsorbable materials suitable for the first and/or second film(s) of anti-adhesive material are chosen from among collagens, oxidized celluloses, polyarylates, trimethylene carbonates, caprolactones, dioxanones, glycolic acid, lactic acid, glycolides, lactides, polysaccharides, for example chitosans, polyglucuronic acids, hyluronic acids, dextrans and their mixtures.

In one embodiment of the present disclosure, the non-bioabsorbable materials suitable for the first and/or second film of anti-adhesive material are chosen from among polytetrafluoroethylene, polyethylene glycols, polysiloxanes, polyurethanes, stainless steels, derivatives of precious metals and their mixtures.

In one embodiment of the present disclosure, the material constituting the first and/or second film(s) of anti-adhesive material is a hydrophilic bioabsorbable material, which may be chosen from the group formed by collagens, polysaccharides and their mixtures. Of the collagens that can be used according to the present disclosure, the following may be mentioned:

1) collagen whose helical structure is at least partially denatured by heat, without hydrolytic degradation, and whose method of preparation is described in WO99/06080,
2) native collagen, not heated, filmed with or without glycerol, crosslinked by gamma irradiation or by other chemical or physical means,
3) and/or their mixtures.

Of the polysaccharides that can be used as absorbable hydrophilic material according to the present disclosure, the following may be mentioned: oxidized cellulose, hyluronic acid, starch, chitosan, crosslinked dextrans and/or their mixtures. All these materials are within the purview of persons skilled in the art. An oxidized cellulose suitable for the present disclosure is the product sold under the brand name "Interceed®" by Ethicon. A hyaluronic acid suitable for the present disclosure is the product sold under the brand name "Hyalobarrier®" by Fidia Advanced Biopolymers, or the product sold under the brand name "Seprafilm®" by Genzyme.

In one embodiment of the present disclosure, the first film and the second film form a single and unique film, the first film then completely coating the first part of the porous structure and thus covering this porous structure part both on its surface intended to face the abdominal cavity and also on its surface intended to face the abdominal wall. Thus, the first part of the porous structure is totally enclosed in the film of anti-adhesive material before implantation and at the moment of implantation.

Thus, at the moment of implantation, and whatever the embodiment of the present disclosure, the two surfaces of the first part of the porous structure are occluded by a continuous film of anti-adhesive material.

The first part of the porous structure of the implant according to the present disclosure, regardless of whether it is totally coated by the first film of anti-adhesive material or whether each of its surfaces are covered, one by the first film of anti-adhesive material, the other by the second film of anti-adhesive material, is thus protected at least during the initial phase of cicatrization, i.e. is not exposed to the inflammatory cells such as granulocytes, monocytes, macrophages, or the multinucleated giant cells that are generally activated by the surgical procedure. Nor is it exposed to the bacteria that may be present. The reason for this is that, at least during the initial phase of cicatrization, which may last approximately 5 to 10 days, only the film or films of anti-adhesive material are accessible to the various factors such as proteins, enzymes, cytokines or inflammatory cells, in the first textile part.

In the case where the film or films of anti-adhesive material are made of non-absorbable materials, they thus protect the first part of porous structure before and after implantation, throughout the period of implantation of the implant.

Furthermore, by virtue of the film or films of anti-adhesive material, the surrounding fragile tissues, such as the hollow viscera for example, are protected in particular from the formation of severe postsurgical fibrous adhesions.

In the case where the anti-adhesive material includes a bioabsorbable material, in embodiments a bioabsorbable material may be chosen that is not absorbed until after a few days, such that the film of anti-adhesive material can perform its function of protecting the stoma organ, for example the intestine, and the hollow organs during the days following the operation, and until the cellular recolonization of the implant in turn protects the fragile organs.

The thickness of the first anti-adhesive film may be less than the thickness E2 of the second part of the porous structure. In fact, the film of anti-adhesive material may not occlude the open surface of the second part of the porous structure, so as to permit cellular recolonization of the second part of the porous structure after implantation.

The first film of anti-adhesive material may be continuous, smooth and non-porous, covering the whole surface of the porous structure intended to be placed facing the abdominal cavity. In one embodiment, the first film of anti-adhesive material extends past the edges of the layer of porous structure. Thus, the implant is protected from contact with the viscera. The first film of anti-adhesive material can, for example, extend past the edges of the layer of porous structure by a distance ranging from about 3 to about 10 millimeters.

The first film of anti-adhesive material may be joined to the surface of the layer of porous structure intended to be placed facing the abdominal cavity by means of surface penetration, keeping open the porosity on the opposite surface of the second part of the porous structure, that is to say the open surface, intended to be placed facing the abdominal wall.

The implant according to the present disclosure can be used via the laparoscopic route. If necessary, for example when the first and second films of anti-adhesive material are made of dried collagen, the implant may be rehydrated at the time of use, in order to make it flexible and easier to use.

The implant according to the present disclosure can, for example, be prepared according to the following method:
a) a textile is prepared that has two-dimensional zones and three-dimensional zones, as has been described above,
b) a solution of an anti-adhesive material is prepared,
c) the solution obtained at b) is poured into a mould,
d) the textile is then applied to the solution, the surface of the textile intended to face the abdominal cavity being placed on the solution in such a way that the solution impregnates the two-dimensional zones of the textile completely,
e) it is left to dry.

With such a method it is possible to obtain an implant according to the present disclosure in which the first film and the second film form a single and unique film.

Alternatively, step d) is replaced by step d') in which the solution of anti-adhesive material only superficially impregnates a single surface of the two-dimensional zones, thereby forming the first film. The procedure is then supplemented by an additional step in which the opposite surface of the two-dimensional zones is impregnated by the same solution of anti-adhesive material or by another solution of another anti-adhesive material in order to form the second film.

Methods of covering/coating that can be used according to the present disclosure are described in documents WO99/06080 and WO2004/043294, the disclosure of which are incorporated herein by this reference in their entirety.

The implant according to the present disclosure can have any shape adapted to the anatomy of the patient and/or to the surgical technique envisaged. For example, the shape of the implant can be round, oval, square or rectangular.

In one embodiment, the implant has a generally elongate shape, for example oval or rectangular. For example, the length of the implant may be from about 12 to about 30 cm and its width may be from about 10 to about 20 cm.

In another embodiment, the implant has a generally round shape. For example, the diameter of the implant may be from about 5 to about 20 cm.

In one embodiment of the present disclosure, the first part of the porous structure has the form of a central strip, and, for example, the width of the central strip may be from about 2 to about 10 cm.

In another embodiment of the present disclosure, the first part of the porous structure has the form of a disc, and, for example, the diameter of the disc may be from about 2 to about 10 cm.

In one embodiment of the present disclosure, at least one orifice is formed at the centre of the first part of the porous structure in order to provide a passage for the stoma organ, for example the intestine, during implantation of the implant. Alternatively, at least one orifice is formed within the first part of the porous structure, the orifice being offset relative to the centre of the implant. For certain types of surgery, for example ureterostomies, the implant can have two orifices. In one embodiment of the present disclosure, the orifice or orifices can be connected to an edge of the implant by way of a slit. For example, the dimensions of the orifices may be from about 0.5 to about 8 cm. The orifice or orifices can be offset relative to the centre of the implant.

BRIEF DESCRIPTION OF THE DRAWINGS

The principles of the present disclosure, and variants thereof, will become evident from the following detailed description and from the attached drawings, in which.

DETAILED DESCRIPTION OF THE EMBODIMENTS

Figure 1:
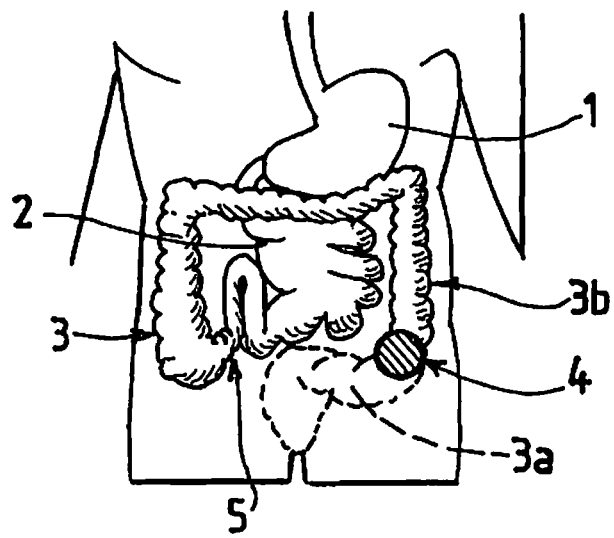
FIG. 1 is a schematic illustration of the human digestive tract, in which a stoma has been formed.
Figure 2:
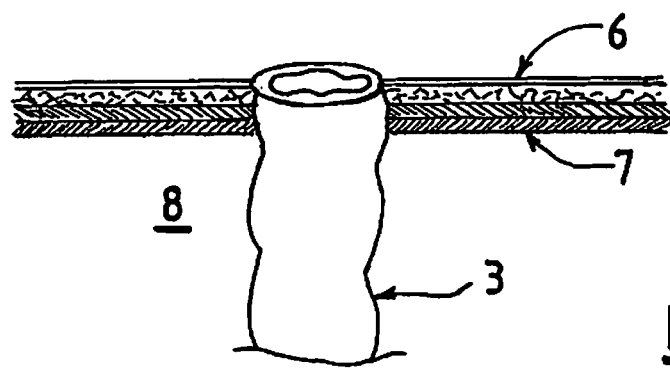
FIG. 2 is a schematic illustration of a direct stoma.
Figure 3:
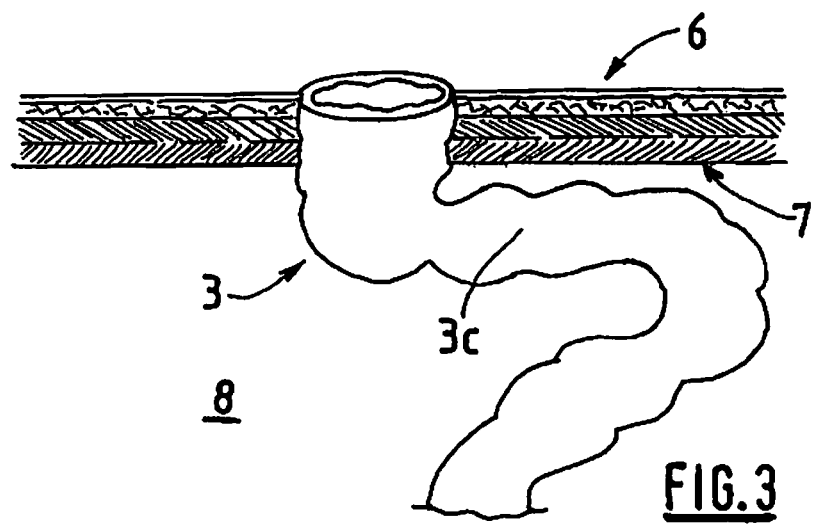
FIG. 3 is a schematic illustration of an indirect stoma.
Figure 4:
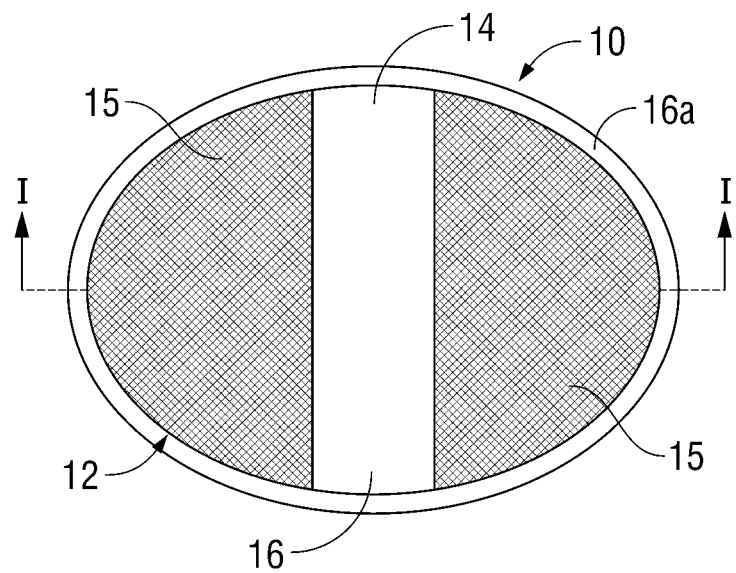
FIG. 4 is a plan view of a first embodiment of an implant according to the present disclosure.
Figure 6:
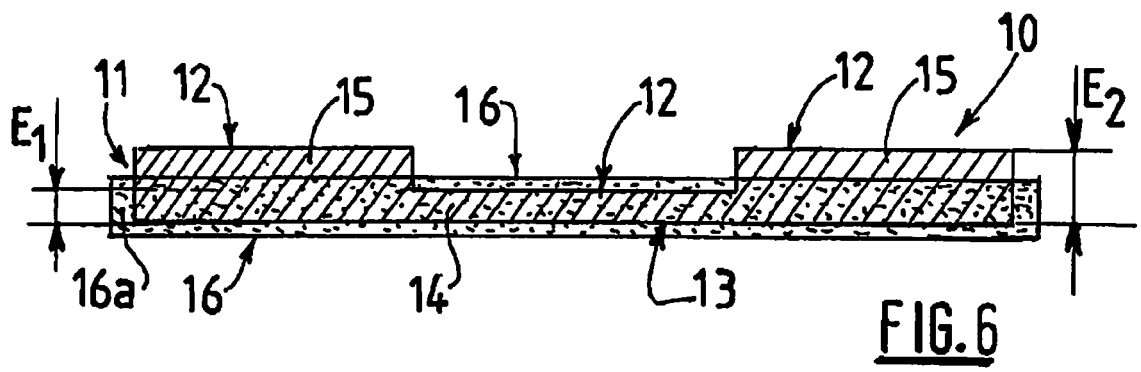
FIG. 6 is a simplified schematic cross-sectional view of the implant from FIG. 4.

Referring to FIGS. 4 and 6, an implant 10 according to the present disclosure is shown which includes a layer of porous structure in the form of a biocompatible textile 11. As will be seen more clearly from FIGS. 13 and 15, the layer of porous structure or textile 11 includes a first surface 12 intended to be placed facing the abdominal wall after implantation, and a second surface opposite the first surface 12, this second surface 13 being intended to be placed facing the abdominal cavity after implantation.

Figure 13:
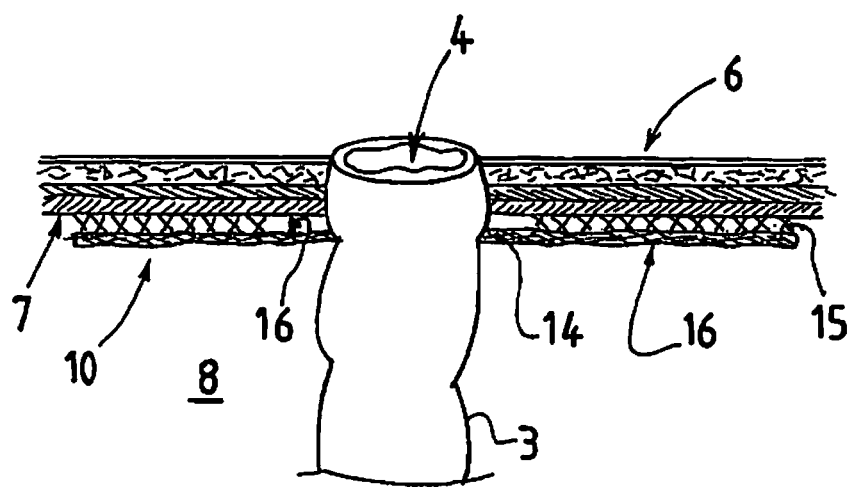
FIG. 13 is a cross-sectional view of an implant according to the present disclosure once it has been implanted after a direct colostomy.
Figure 14:
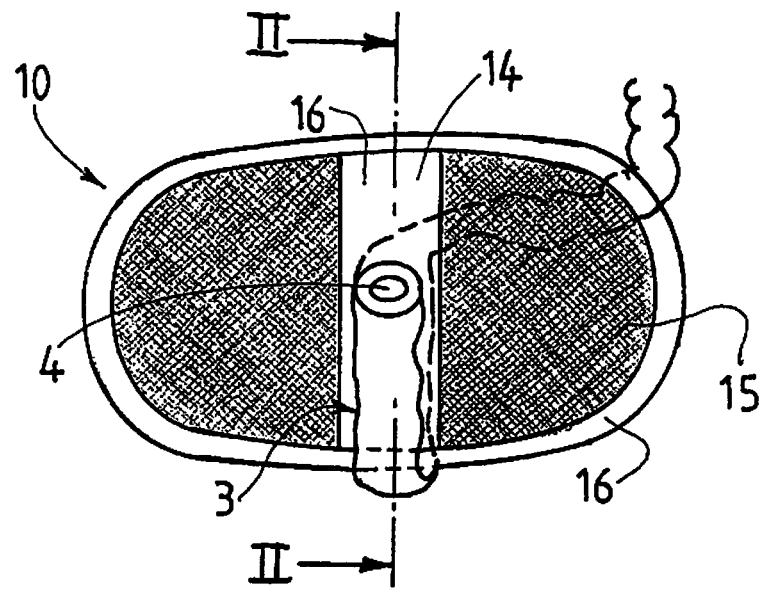
FIG. 14 is a schematic plan view of another embodiment of an implant according to the present disclosure once it has been implanted after an indirect colostomy.
Figure 15:
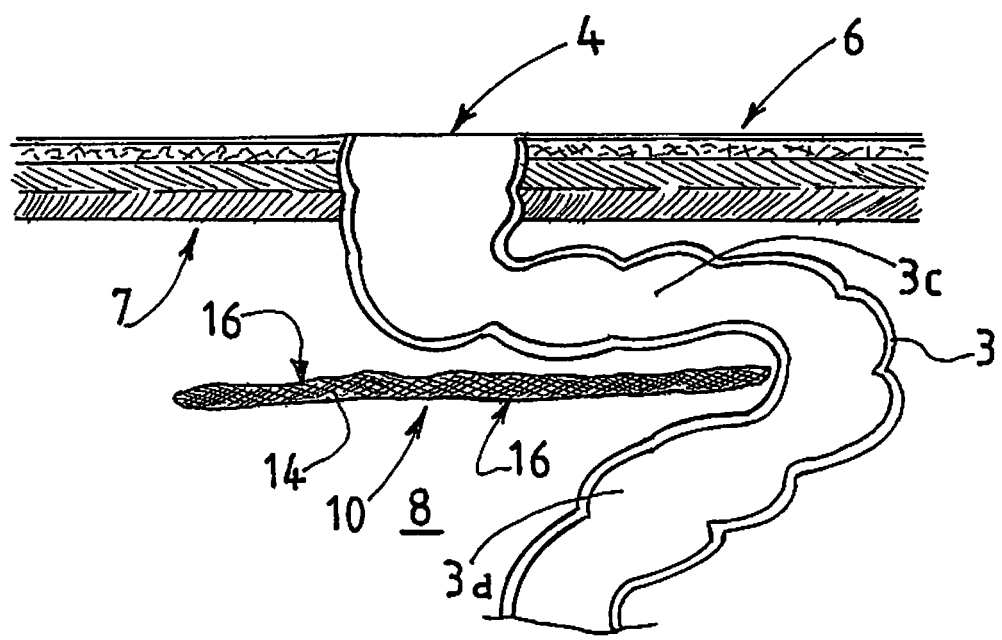
FIG. 15 is a cross-sectional view of the implant from FIG. 14 along the line 11 in FIG. 14.

As seen in FIG. 4, which is a plan view of an implant according to the is present disclosure, the layer of porous structure includes a first textile part 14 and a second textile part 15, the first textile part and the second textile part together forming the biocompatible textile 11 (see FIG. 6). As seen in FIGS. 13-15 regarding the first surface 12 of the biocompatible textile 11, the first part 14 of textile is able to come into contact with the intestine, and the second part 15 of textile is intended to be placed facing the abdominal wall once the implant 10 according to the present disclosure is implanted in the patient.

The implant 10 shown in FIG. 4 is oval in shape. Its length may be, for example, from about 15 to about 30 cm, and its width may be, for example, from about 12 to about 20 cm. The shape of the implant can be adapted to the anatomy of the patient. It can also vary depending on the surgical technique envisaged.

In one example not shown, the implant has a generally round shape. Its diameter may then be from about 5 to about 20 cm, for example.

Referring to FIG. 6, the implant 10 according to the present disclosure is covered on its second surface 13 by a film 16 of anti-adhesive material. The edge 16a of the film of anti-adhesive material extends past the second surface 13 of the textile 11, for example by a distance of from about 3 to about 10 mm. Thus, the implant 10 is protected from contact with the viscera when it is implanted.

FIG. 6 is a simplified cross-sectional view of the implant from FIG. 4 along line II. As shown in FIG. 6, the first part 14 of the textile and the second part 15 of the textile each have a thickness, namely a thickness E1 and a thickness E2, respectively. The value of the thickness E2 of the second part 15 of the textile is superior to the value of the thickness E1 of the first part 14 of the textile. Moreover, the film 16 completely encompasses the first part 14 of textile but only penetrates superficially into the thickness E2 of the second part 15 of the textile. It must be understood that the film 16 penetrates into the second part 15 of textile only by a short distance, for example by a distance corresponding to about 2% to about 10% of the thickness E2. In the example shown, the value of the thickness E1 is about 0.75 mm, while that of the thickness E2 is about 2.00 mm.

Thus, as seen in FIG. 6, the first part 14 of the textile is covered by film 16 of anti-adhesive material on its two surfaces, and this first part 14 of textile is totally enclosed within the film 16 of anti-adhesive material.

By contrast, in regards to the second part 15 of the textile, its first surface 12, intended to be placed facing the abdominal wall, is not covered by film 16 of anti-adhesive material. This surface 12 will be referred to hereinbelow as the open surface of the second part 15 of the textile. By contrast, the second surface 13 intended to be placed facing the abdominal cavity, is covered by film 16 of anti-adhesive material. This surface 13 will be referred to hereinbelow as the closed surface of the second part of the textile. Thus, the film 16 of anti-adhesive material penetrates only superficially into the second part 15 of the textile, in the area of its closed surface 13, leaving open the porosity of the first open surface 12 of the second textile part 15.

Figure 7:
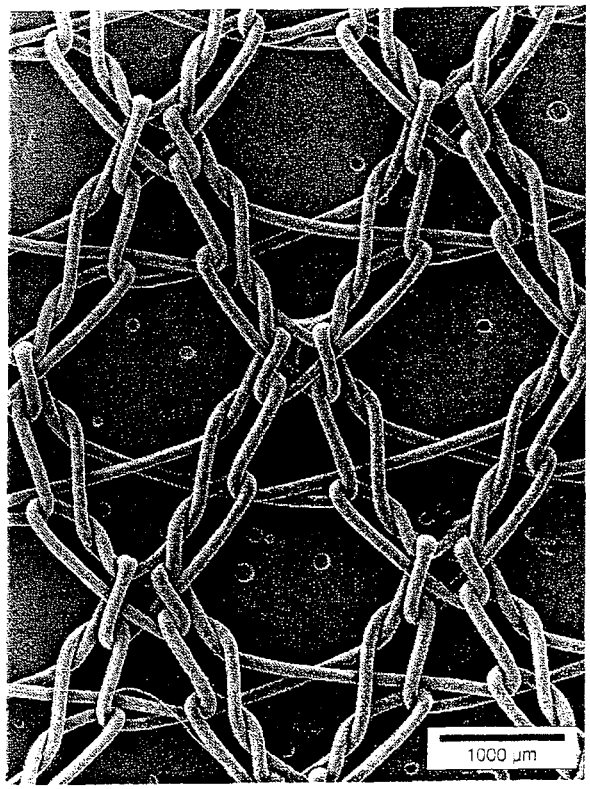
FIG. 7 is a photograph taken with a Hitachi S-800 FEG scanning electron microscope, magnification x40, showing an embodiment of the first part of the porous structure of an implant according to the present disclosure.
Figure 10:
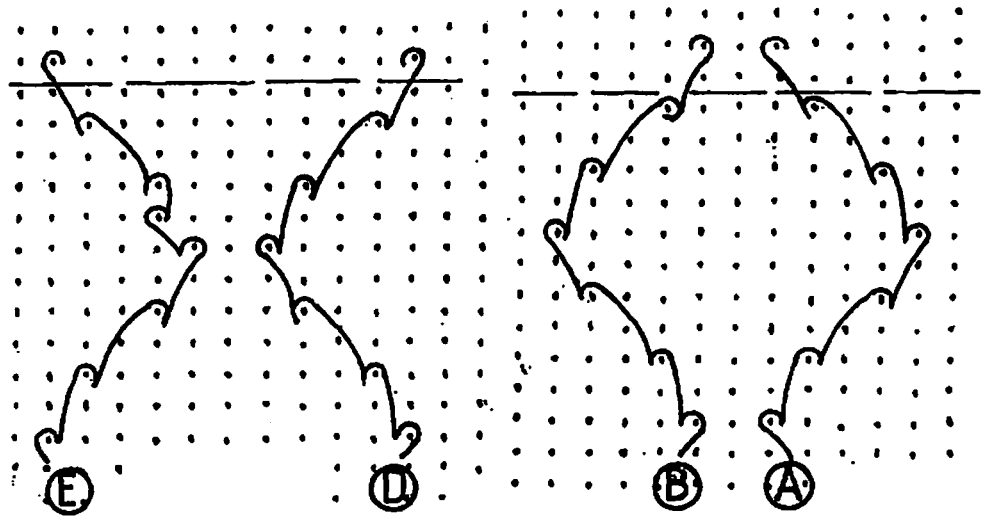
FIGS. 10, 10A, 11 and 12 show embodiments of the knitting structure suitable for producing a textile for an implant according to the present disclosure.

FIG. 7 shows a view of the first part 14 of textile. In this example, the first part of the textile is a knit obtained on a warp knitting machine or raschel machine with two guide bars A and B, threaded regularly with one guide full, one guide empty, using the knitting structure shown in FIG. 10 for bars A and B. The respective charts used for bars A and B are the following:

Bar A: 4-4-5-4/4-4-4-3/3-3-2-1/1-1-0-1/1-1-1-2/2-2-3-4//
Bar B: 1-1-0-1/1-1-1-2/2-2-3-4/4-4-5-4/4-4-4-3/3-3-2-1//

The yarn used may be a monofilament yarn of polyethylene terephthalate, having a diameter of about 0.08 mm and a titre of about 69 dtex. The knit thus formed includes two opposite surfaces but is free of connecting sheets between its two opposite surfaces. It is a two-dimensional knit according to the present application.

The thickness of the first part of the textile formed from such a knit is approximately 0.25 mm.

In the example shown, the knitting used for the first part of the textile creates pores, in embodiments with dimensions that can range from about 0.1 to about 3 mm, in embodiments from about 1.5 to about 2 mm. At the moment of implantation, these pores are not visible, nor are they accessible to tissue colonization, because the whole of the first part of the textile is confined in the film 16 of anti-adhesive material. However, after a few days, as the film of anti-adhesive material is absorbed and disappears after performing its function of limiting and/or avoiding formation of adhesions during the first 10 days following the implantation operation, the pores of the first part 14 of the textile become accessible to tissue colonization. When a yarn of polyethylene terephthalate is used for producing the two-dimensional knit, this knit is non-bioabsorbable and remains permanently at the implantation site.

In another embodiment of the present disclosure, the first part 14 of the textile is made of a bioabsorbable material that is absorbed more slowly than the bioabsorbable material constituting the film 16 of anti-adhesive material.

Figure 8:
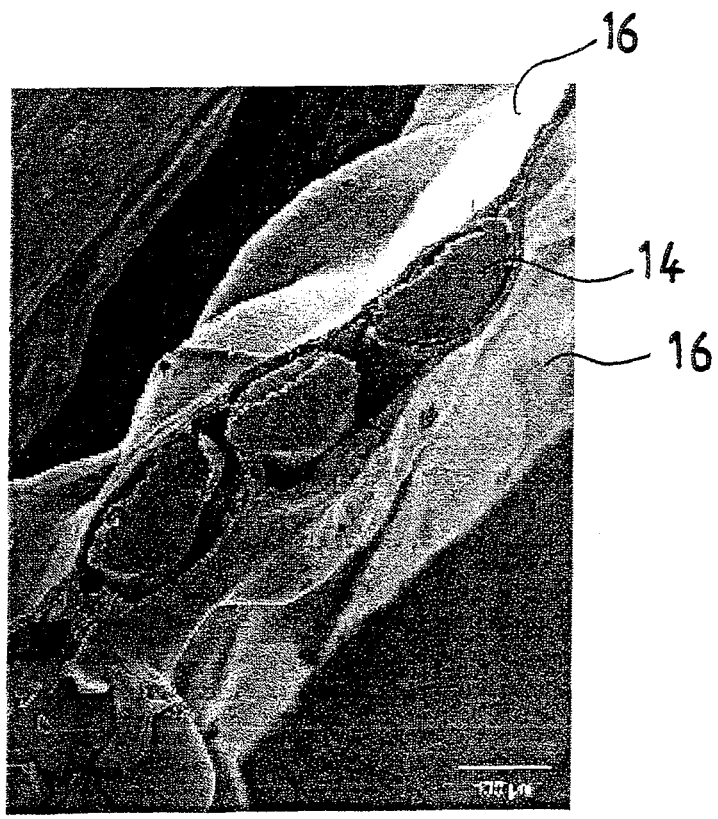
FIG. 8 is a photograph taken with a Hitachi S-800 FEG scanning electron microscope, magnification x250, showing the first part of the porous structure from FIG. 7 once enclosed in the film of anti-adhesive material.

As is shown in FIG. 8, which is a scanning electron microscope photograph of a section of the implant according to one embodiment of the present disclosure in the area of the first textile part, the latter is enclosed in the film 16 of anti-adhesive material. The coating of the first part 14 of textile by the film 16 of anti-adhesive material can be effected using any method known to a person skilled in the art. In the example shown in FIG. 8, the first part 14 of textile is coated using the method described in the application WO2004/043294.

Thus, as will be seen clearly from FIG. 8, the first part 14 of the textile is covered by the film of anti-adhesive material on its two surfaces, and the porosity (see FIG. 7) of the first part of the textile is occluded at the moment of implantation. Thus, once covered with a film 16 of anti-adhesive material, the two surfaces of the first part 14 of textile are smooth and non-porous, as shown in FIG. 8. The two surfaces of the first part 14 of textile do not damage the organs situated in the proximity of this first part 14 of textile, particularly the stoma organs.

The second part 15 of the textile, of which the thickness is greater than that of the first part 14 of the textile, can be a knit which is obtained on a warp knitting machine or double-bed raschel machine and which has two opposite surfaces connected to each other by connecting yarns, that is to say a three-dimensional knit according to the present application. For example, a first surface of the knit is produced with the two guide bars A and B already mentioned above for producing the first part 14 of textile, these being threaded identically and with the same charts as above. The second surface of the knit is produced with two supplementary guide bars D and E, threaded with one guide full, one guide empty, using the knitting structure shown in FIG. 10 for bars D and E. The respective charts used for bars D and E are the following:
Bar D: 0-1-1-1/1-2-2-2/3-4-4-4/5-4-4-4/4-3-3-3/2-1-1-1//
Bar E: 5-4-4-4/4-3-3-3/2-1-1-1/0-1-1-1/1-2-2-2/3-4-4-4//

Figure 10A:
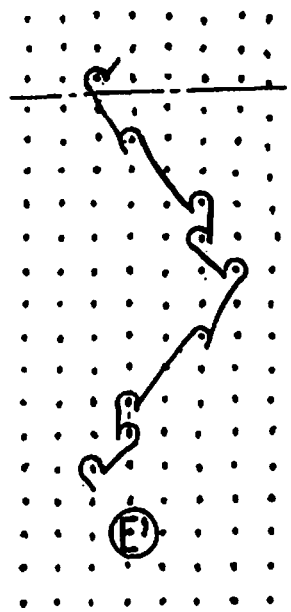

The connection of the two surfaces can be effected, for example, by hooking one loop in two, or in three, or in four, or in five, or in six of one of the bars D or E, whose knitting structure will be adapted. For example, in one embodiment of the present disclosure, the connection of the two surfaces is effected by hooking one loop in three of the bar E, which thus becomes bar E', with the knitting structure shown in FIG. 10A and according to the following chart:
Bar E': 5-4-3-4/4-3-3-3/2-1-1-1/0-1-2-1/1-2-2-2/3-4-4-4//

Figure 11:

In another embodiment, the connection of the two surfaces can be effected with the aid of a fifth guide bar C, with the knitting structure shown in FIG. 11 and according to the following chart:
Bar C: 1-0-1-0/1-1-1-1/1-1-1-1//

Figure 5:
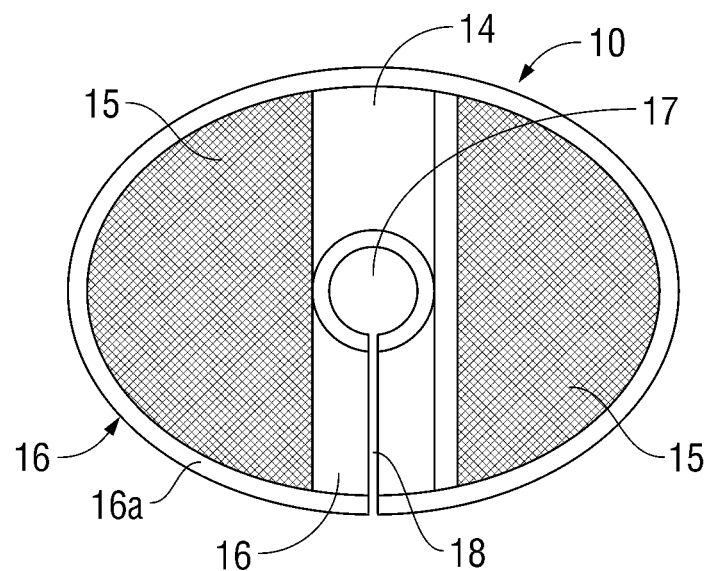
FIG. 5 is a plan view of a second embodiment of an implant according to the present disclosure.

Thus, when the first part 14 of the textile is in the form of a central strip separating two lateral strips of the second part 15 of the textile, as is shown in FIGS. 4 and 5, the textile 11 can be produced in one piece, on the same knitting machine.
With the guide bars A, B, D and E' described above:
the whole of the first surface 13 of the textile 11 is produced with the two guide bars A and B,
along a first length, corresponding to the first lateral strip of the second part 15 of the textile, the guide bars D and E' are threaded one guide full, one guide empty, in order to produce the second surface of the three-dimensional knit forming the second part 15 of the textile,
then, along the length corresponding to the width of the central strip of the first part 14 of the textile, the guide bars D and E' are left empty in order to form the two-dimensional knit,
finally, along a length corresponding to the second lateral strip of the second part 15 of the textile, the guide bars D and E' are again threaded one guide full, one guide empty, in order to produce the second surface of the three-dimensional knit forming the second part 15 of the textile.

In such a case, the optional fifth guide bar C is threaded only in the zones of the three-dimensional knit.

Figure 12:
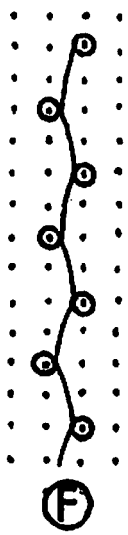

Finally, in order to obtain a smooth join between the three-dimensional knit forming the second part 15 of the textile and the two-dimensional knit forming the first part 14 of the textile, it is possible to use, still on the same knitting machine, a supplementary guide bar F in order to finish the edges of the three-dimensional knits, threaded in the area of these edges, according to the knitting structure shown in FIG. 12, using the following chart for example:
Bar F: 1-0-1-1/1-2-1-1//

A monofilament yarn may be chosen to produce the second part 15 of the textile. This is because multifilament yarns may pose greater risks of bacteria developing in the interstices present between the various filaments of the yarn.

The yarn used may be a monofilament yarn of polyethylene terephthalate, with a diameter of approximately 0.08 mm and titre of approximately 69 dtex.

The thickness of the second part 15 of the textile, produced in the form of the three-dimensional knit described above, is approximately 1.50 mm.

Figure 9:
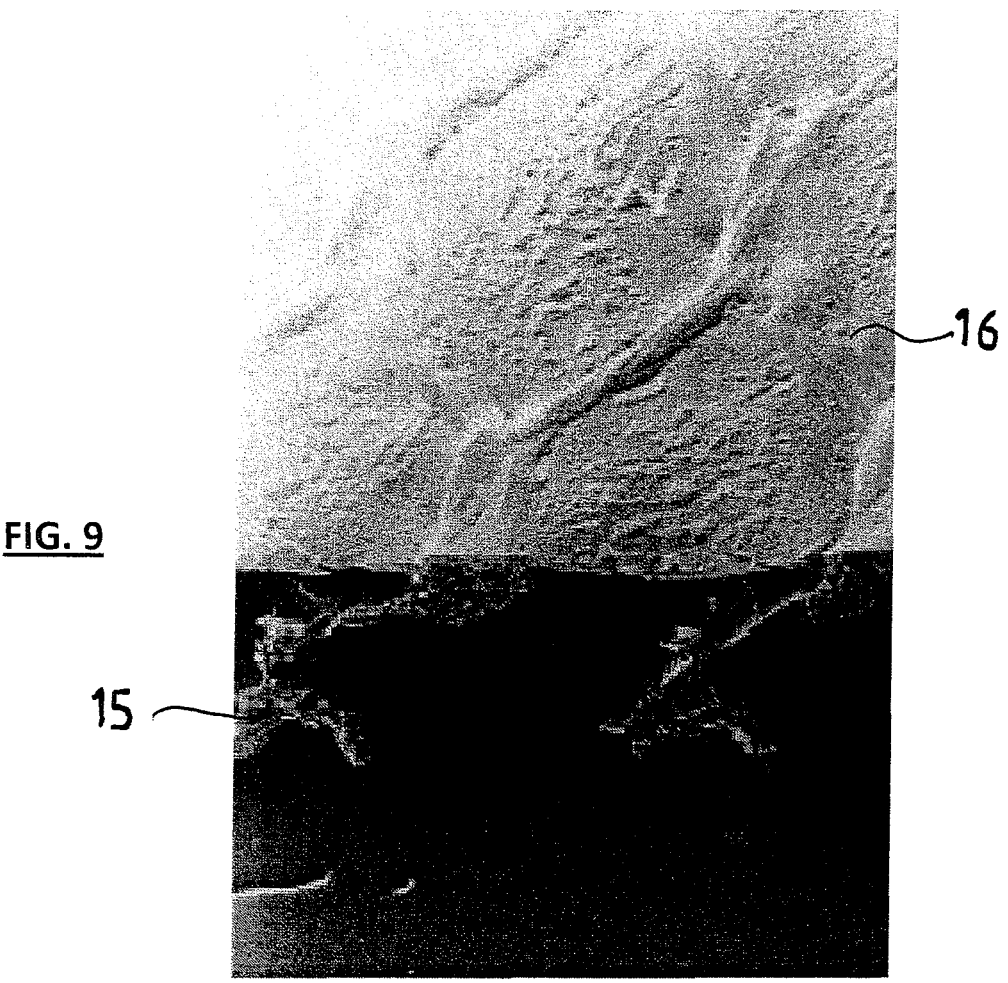
FIG. 9 is a photograph taken with a Hitachi S-800 FEG scanning electron microscope, magnification x20, showing an embodiment of the second part of the porous structure of an implant according to the present disclosure, covered on one surface by the first film of anti-adhesive material.

As will be seen from FIG. 9, the second part 15 of the textile is covered, on its surface intended to face the abdominal cavity, by the film 16 of anti-adhesive material. The film 16 of anti-adhesive material penetrates only superficially into the three-dimensional knit forming the second part 15 of textile. Consequently, the surface of the second part 15 of textile intended to face the abdominal wall is open, and its porosity is not occluded. This open surface therefore promotes all cellular growth.

The superficial covering of the surface of the second part 15 of textile intended to be placed facing the abdominal cavity can be carried out using any method within the purview of a person skilled in the art, for example using the method described in the application WO99/06080.

The material used for the film 16 of anti-adhesive material can, for example, be collagen prepared in the manner described in the application WO99/06080.

The film 16 of anti-adhesive material may be applied to the surface of the textile 11 intended to be placed facing the abdominal cavity, in the following way:

The solution of collagen is poured into a mould having the external dimensions desired for the film. The textile produced above is then applied to this solution, at the centre of the mould, the surface to be covered being placed on the solution of collagen. The solution of collagen then penetrates into the textile by capillary force, completely coating the first part of textile and covering the latter on the two opposite surfaces of the two-dimensional knit forming it, and penetrating only by a small distance into the thickness of the second part of textile, thus creating a superficial film for this three-dimensional part. Once the collagen has dried, the film is cut around the textile using a scalpel.

Alternatively, the covering/coating method described in WO2004/043294 can be used.

In another embodiment not shown here, the film 16 only superficially covers the surface of the first part of the textile, intended to be placed facing the abdominal cavity, and does not encompass the two opposite surfaces of this first part of the textile. In such a case, the surface of the first part of the textile intended to be placed facing the abdominal wall is covered with a second film of anti-adhesive material. Thus, each of the two opposite surfaces of the first part of the textile is covered by a smooth and continuous film of anti-adhesive material. Covering methods that can be used to form this second film are also described in WO2004/043294.

FIG. 13 shows an implant according to the present disclosure after it has been implanted, in the case of a direct stoma. To do this, the implant according to the present disclosure shown in FIG. 5 is used for example. In this figure, the reference numbers designating the same elements as in FIG. 4 have been retained. The implant 10 in FIG. 5 includes an orifice 17 which has been created at about the centre of the implant 10 and at about centre of the central strip formed by the first part 14 of the textile. Such an orifice 17 can have a diameter ranging from about 1 to about 8 cm. A slit 18 starting from the central orifice 17 and opening out on an edge of the implant 10 allows the implant to be adjusted around the colon 3 during implantation of the implant.

In one embodiment not shown here, the orifice 17 is offset relative to the centre of the implant 10. It is also possible to have several orifices, depending on the surgery envisaged.

Thus, in FIG. 13, an implant 10 similar to that in FIG. 5 has been placed around the colon 3, which is at substantially right angles to the abdominal wall 7 and to the skin 6. As shown in this figure, the first part 14 of the textile is covered entirely, that is to say on its two opposite surfaces, by the film 16 of anti-adhesive material is situated in direct proximity to the colon 3. Thus, the colon 3, which is a fragile organ, is not damaged by the implant 10. The open surface of the second part 15 of the textile, which is porous and promotes cellular recolonization, is situated facing the abdominal wall 7. Thus, after implantation, the cells of the abdominal wall can gradually colonize the second part 15 of textile, for example the three-dimensional knit forming it.

It is possible to fix the implant 10 to the abdominal wall 7 using staples or sutures. In addition, or alternatively, the open surface of the second part 15 of the textile can intrinsically include barbs or loops, which will facilitate its natural attachment to the abdominal wall. Such an affixing knit is described in the application WO01/81667.

Finally, the second surface of the textile, completely covered by film 16 of anti-adhesive material, is situated facing the abdominal cavity 8. Thus, the hollow and fragile organs, the viscera, are not damaged by the implant.

FIGS. 14 and 15 show an implant according to the present disclosure after it has been implanted, in the case of an indirect stoma. To do this, the implant according to the present disclosure in FIG. 4 is used, for example. FIG. 14 shows a plan view of the implant 10 according to FIG. 4 at its implantation site in the area of the colon 3. For greater clarity, the skin and the abdominal wall have not been depicted. As will be seen from FIG. 15, which is a cross-sectional view of FIG. 14 along line II-II and in which the abdominal wall 7 and the skin 6 have been depicted, the colon 3 forms a bend prior to exteriorization, and the implant 10 is placed inside this bend. A part 3c of the colon is thus situated between the implant 10 and the abdominal wall 7.

As will be seen from these two figures, the part 3c of the colon faces and is able to come into contact with the first part 14 of the textile covered on its two opposite surfaces by the film 16 of anti-adhesive material. Thus, neither the part 3c of the colon, situated between the implant 10 and the abdominal wall 7, nor the part 3d of the colon corresponding to the second length of the bend and able to lie under the implant 10 in the area of the abdominal cavity 8, risks being damaged by the implant 10. This is because the parts 3c and 3d of the colon 3 are each facing a surface of the first part 14 of textile covered by a film 16 of anti-adhesive material. Moreover, the relatively small thickness E1 of this first part 14 of textile permits flexible and atraumatic support of the colon 3.

In an indirect stoma of this kind, the implant 10 may act like a hammock for the part 3c of the colon 3, and the implant 10 can be fixed to the abdominal wall 7 via the open surface of the second part 15 of the textile placed facing the abdominal wall 7.

The present disclosure also relates to a method for treatment or prevention of a hernia in the proximity of a stoma formed in the skin, including the step of implanting an implant of the type described above in the area of the stoma. In one embodiment of the present disclosure, the implant is fixed to the abdominal wall. The implant described above can be implanted by open surgery or by laparoscopy.

The implant according to the present disclosure is used in particular in the treatment of parastomal hernias. It is able to support and/or protect the organs that are to be treated, such as the colon or ureters, without damaging them, while at the same time effectively strengthening the wall in which the stoma is formed, such as the abdominal wall, irrespective of the type of stoma formed, i.e. direct stoma or indirect stoma.

What is claimed is:

1. An implant for the prevention or treatment of a hernia formed in an abdominal wall in the proximity of a stoma of an organ comprising: a porous structure including a surface intended to face an abdominal cavity covered by a first film of anti-adhesive material, the porous structure comprising a first part intended to be in contact with a stoma organ and having a first thickness, and a second part having a second thickness greater than the first thickness, the first part and the second part including a surface intended to face an abdominal wall, the surface of the first part being covered by a second film of anti-adhesive material, and the surface of the second part having an open surface.

2. The implant according to claim 1, wherein the porous structure comprises a sponge, a fibrous matrix, or a combination of a sponge and of a fibrous matrix.

3. The implant according to claim 2, wherein the porous structure comprises a textile.

4. The implant according to claim 3, wherein the first part of the porous structure is composed of yarns made of biocompatible materials, bioabsorbable materials, non-bioabsorbable materials and their mixtures.

5. The implant according to claim 4, wherein the bioabsorbable materials are chosen from among polylactic acid (PLA), polysaccharides, polycaprolactones (PCL), polydioxanones (PDO), trimethylene carbonates (TMC), polyvinyl alcohol (PVA), polyhydroxyalkanoates (PHA), polyamides, polyethers, oxidized cellulose, polyglycolic acid (PGA), copolymers of these materials and their mixtures.

6. The implant according to claim 4, wherein the non-bioabsorbable materials are chosen from among polypropylenes, polyesters such as polyethylene terephthalates, polyamides, polyvinylidene fluoride, and their mixtures.

7. The implant according to claim 4, wherein the yarns forming the first part of the porous structure are chosen from among monofilament yarns, multifilament yarns and their combinations.

8. The implant according to claim 7, wherein the yarns forming the first part of the porous structure are monofilament yarns.

9. The implant according to claim 8, wherein the monofilament yarns have a diameter of from about 0.06 to about 0.15 mm.

10. The implant according to claim 8, wherein the monofilament yarns are of polyethylene terephthalate.

11. The implant according to claim 3, wherein the second part of the porous structure is composed of yarns made of biocompatible materials, bioabsorbable materials, non-bioabsorbable materials and their mixtures.

12. The implant according to claim 11, wherein the bioabsorbable materials are chosen from among polylactic acid (PLA), polysaccharides, polycaprolactones (PCL), polydioxanones (PDO), trimethylene carbonates (TMC), polyvinyl alcohol (PVA), polyhydroxyalkanoates (PHA), polyamides, polyethers, oxidized cellulose, polyglycolic acid (PGA), copolymers of these materials and their mixtures.

13. The implant according to claim 11, wherein the non-bioabsorbable materials are chosen from among polypropylenes, polyesters such as polyethylene terephthalates, polyamides, polyvinylidene fluoride, and their mixtures.

14. The implant according to claim 11, wherein the yarns forming the second part of the porous structure are chosen from among monofilament yarns, multifilament yarns and their combinations.

15. The implant according to claim 14, wherein the yarns forming the second part of the porous structure are monofilament yarns.

16. The implant according to claim 15, wherein the monofilament yarns have a diameter of from about 0.06 to about 0.15 mm.

17. The implant according to claim 15, wherein the monofilament yarns are of polyethylene terephthalate.

18. The implant according to claim 1, wherein the porous structure has pores with dimensions of from approximately 0.1 to approximately 3 mm.

19. The implant according to claim 1, wherein the first thickness is from approximately 0.15 to approximately 0.50 mm.

20. The implant according to claim 1, wherein the first part of the porous structure is a textile in the form of a two-dimensional knit.

21. The implant according to claim 20, wherein the second part of the porous structure is a textile in the form of a three-dimensional knit.

22. The implant according to claim 21, wherein the two-dimensional knit and the three-dimensional knit are joined together by at least one seam.

23. The implant according to claim 21, wherein the two-dimensional knit and the three-dimensional knit are knitted together on the same knitting machine and constitute a textile made in one piece.

24. The implant according to claim 1, wherein the second thickness is from about 0.40 to about 3.00 mm.

25. The implant according to claim 1, wherein the second part of the porous structure includes a surface intended to face the abdominal wall having elements chosen from loops, barbs, hooks, threads, or clips for fastening the second part to the abdominal wall.

26. The implant according to claim 25, wherein the elements are chosen from among loops, barbs, and their mixtures.

27. The implant according to claim 1, wherein the anti-adhesive material of the first and/or second film is chosen from among bioabsorbable materials, non-bioabsorbable materials and their mixtures.

28. The implant according to claim 27, wherein the bioabsorbable materials are chosen from among collagens, oxidized celluloses, polyarylates, trimethylene carbonates, caprolactones, dioxanones, glycolic acid, lactic acid, glycolides, lactides, polysaccharides, for example chitosans, polyglucuronic acids, hylauronic acids, dextrans and their mixtures.

29. The implant according to claim 27, wherein the non-bioabsorbable materials are chosen from among polytetrafluoroethylene, polyethylene glycols, polysiloxanes, polyurethanes, stainless steels, derivatives of precious metals and their mixtures.

30. The implant according to claim 29, wherein the bioabsorbable material is a hydrophilic material chosen from the group consisting of collagens, polysaccharides and their mixtures.

31. The implant according to claim 1, wherein the first film of anti-adhesive material extends past the edges of the porous structure.

32. The implant according to claim 31, wherein the first film of anti-adhesive material extends past the edges of the porous structure by about 3 to about 10 millimeters.

33. The implant according to claim 1, wherein the first film and the second film form a single film, the first film completely coating the first part of the porous structure and thus covering the first part of the porous structure both on the surface intended to face the abdominal cavity and also on the surface intended to face the abdominal wall.

34. The implant according to claim 1, wherein the porous structure has a generally elongate shape.

35. The implant according to claim 1, wherein the porous structure has a generally round shape.

36. The implant according to claim 1, wherein the first part of the porous structure has a central strip.

37. The implant according to claim 36, further comprising at least one orifice formed at about centre of the first part of the porous structure to provide a passage for the stoma organ during implantation of the implant.

38. The implant according to claim 36, further comprising at least one orifice formed within the first part of the porous structure, the orifice being offset relative to the centre of the implant.

39. The implant according to claim 1, wherein the first part of the porous structure has a disc shape.

40. A method of treating or preventing a hernia in the proximity of a stoma formed in the skin comprising: implanting an implant according to claim 1 in the proximity of a stoma, the porous structure including a surface intended to face an abdominal cavity covered by a first film of anti-adhesive material, the porous structure comprising a first part intended to be in contact with a stoma organ and having a first thickness, and a second part having a second thickness greater than the first thickness, the first part including a surface intended to face an abdominal wall covered by a second film of anti-adhesive material.

* * * * *